United States Patent

Harken et al.

[11] 3,972,922
[45] Aug. 3, 1976

[54] PROCESS FOR PREPARING ETHER TRICARBOXYLATES

[75] Inventors: Russel D. Harken, Maryland Heights; F. Wyman Morgan, Ballwin, both of Mo.

[73] Assignee: Monsanto Company, St. Louis, Mo.

[22] Filed: Mar. 18, 1974

[21] Appl. No.: 452,308

[52] U.S. Cl. .................. 260/535 P; 260/340.6; 260/484 P
[51] Int. Cl.² ........................................ C01C 59/12
[58] Field of Search ........................... 260/535 P

[56] References Cited
OTHER PUBLICATIONS

E. von Rudloff, Canadian J. of Chemistry, vol. 35, pp. 315–321, 1957.

*Primary Examiner*—Paul J. Killos
*Attorney, Agent, or Firm*—J. E. Maurer; N. E. Willis; T. N. Wallin

[57] ABSTRACT

Sequestrant compounds represented by the

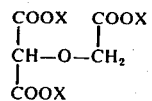

wherein X is alkali metal or hydrogen, are prepared by oxidation of a compound represented by the formula

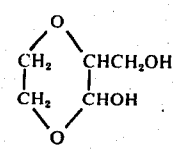

3 Claims, No Drawings

PROCESS FOR PREPARING ETHER TRICARBOXYLATES

BACKGROUND OF THE INVENTION

This invention relates to novel processes for making ether tricarboxylates represented by the formula

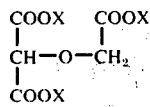

wherein X is alkali metal or hydrogen.

It is known that such ether tricarboxylates (in salt form) are useful as complexing agents for metal and alkaline earth metal ions and as detergency builders whereas the acid forms are useful intermediates for their synthesis. Although methods for synthesis of such compounds (e.g., via Williamson ether type synthesis) have been disclosed, alternate processes for their preparation are desired.

SUMMARY OF THE INVENTION

This invention provides a process for preparation of the above-described ether tricarboxylates by oxidation of a compound represented by the formula

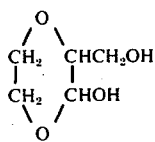

The process will be understood from the following description of the preferred embodiments.

DESCRIPTION OF THE PREFERRED EMBODIMENTS

In the process of this invention, 2-hydroxy-3-hydroxymethyl-1,4-dioxane

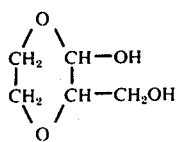

is oxidized to yield

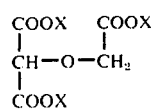

For example, the oxidation can be accomplished using $CrO_3$, preferably dissolved in $H_2SO_4$, as an oxidizing agent. This reaction yields the ether tricarboxylic acid which can be esterified by conventional procedures to facilitate isolation of the ester by conventional solvent extraction procedures, e.g., with chloroform. The ester form of the ether tricarboxylate is readily converted to the salt form by reaction with alkali metal hydroxide.

Oxidation conducted under basic conditions will yield the salt forms of the ether tricarboxylate directly.

The 2-hydroxy-3-hydroxymethyl-1,4-dioxane used in the above reaction can be prepared by a Prins reaction wherein formaldehyde is reacted with p-dioxene (a known compound whose synthesis is described by Moss and Paige, J. Eng. Chem. Data, 12, 452 (1967)). In this reaction, acid, e.g., sulfuric acid, is added to formaldehyde and p-dioxene combined with the mixture. The acid catalyst can then be neutralized, e.g., with sodium carbonate, and water removed by evaporation to leave the desired product. Preferably the temperature of the reaction is maintained below 40°C. The amount of acid catalyst used for given reaction conditions can be optimized by routine tests. Generally, increasing catalyst concentration increases by-product formation whereas decreasing the concentration lowers the reaction rate.

The invention is further illustrated by the following example wherein all parts and percentages are by weight unless otherwise indicated.

EXAMPLE I

About 129 grams p-dioxene is added slowly to a mixture of 2.7 grams sulfuric acid and 130 grams 37% formalin (a solution of formaldehyde in water). During addition the mixture is maintained below 40°C. The mixture is stirred for about 14 hours and then neutralized to pH 7 with saturated $Na_2CO_3$ solution. The solution is concentrated by evaporation of water and filtered to separate $Na_2SO_4$.

About 2 grams of the resulting concentrated 2-hydroxy-3-hydroxy-methyl-1,4-dioxane is dissolved in 3 grams water and added to a mixture of 7.5 grams $CrO_3$, 22 grams $H_2SO_4$ and 33.7 grams $H_2O$ cooled to 0°C. Exothermic oxidation is complete in a few minutes yielding

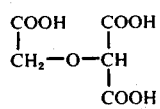

The mixture is extracted with an ethanol-benzene mixture to strip off water and convert the acid to the corresponding ester.

Crystalline $Cr_2(SO_4)_3$ is removed by filtration and the ester isolated by extraction with chloroform.

The chloroform is evaporated and the ester is converted to

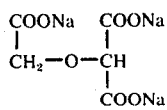

by reaction with sodium hydroxide.

What is claimed is:

1. A process for making compounds represented by the formula

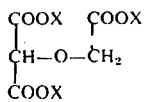

wherein X is alkali metal or hydrogen said process comprising oxidizing a compound represented by the formula

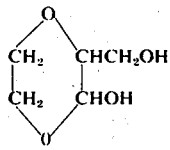

said oxidation being conducted utilizing an oxidizing agent having an oxidation potential at least equivalent to that of $CrO_3$.

2. The process of claim 1 wherein the oxidation is conducted in acid medium to yield the ether tricarboxylic acid

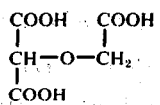

and further comprising converting said ether tricarboxylic acid to the salt

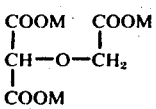

wherein M is alkali metal.

3. The process of claim 2 wherein the oxidation is conducted using $CrO_3$ as an oxidizing agent and the ether tricarboxylic acid is esterified and the resulting ester reacted with alkali metal hydroxide.

* * * * *